United States Patent [19]
Tsai et al.

[11] Patent Number: 5,462,695
[45] Date of Patent: Oct. 31, 1995

[54] CHIRAL LIQUID CRYSTAL MATERIALS AS DOPANT FOR FERROELECTRIC LIQUID CRYSTAL COMPOSITIONS

[75] Inventors: Wen-Liang Tsai, Tainan; Chein-Dhau Lee, Hsinchu, both of Taiwan

[73] Assignee: Industrial Technology Research Institute, Hsinchu, Taiwan

[21] Appl. No.: 269,793

[22] Filed: Jun. 30, 1994

[51] Int. Cl.⁶ .......................... C09K 19/12; C09K 19/20; C07C 69/76
[52] U.S. Cl. ................ 252/299.65; 252/299.64; 252/299.66; 252/299.67; 560/59; 560/61; 560/76
[58] Field of Search .............. 252/299.1, 299.64, 252/299.65, 299.66, 299.5; 560/59, 61, 76

[56] References Cited

U.S. PATENT DOCUMENTS

| | | | |
|---|---|---|---|
| 4,923,633 | 5/1990 | Gray et al. | 252/299.65 |
| 5,130,048 | 7/1992 | Wand et al. | 252/299.01 |
| 5,356,564 | 10/1994 | Tsai et al. | 252/299.64 |
| 5,360,575 | 11/1994 | Tsai et al. | 252/299.01 |
| 5,366,656 | 11/1994 | Tsai et al. | 252/299.01 |
| 5,366,659 | 11/1994 | Tsai et al. | 252/299.61 |

*Primary Examiner*—Shean Wu
*Attorney, Agent, or Firm*—W. Wayne Lianh

[57] ABSTRACT

Chiral liquid crystal compounds for use as dopants to be mixed with a liquid crystal host material, which may or may not be composed of chiral molecules, to form ferroelectric liquid crystal compositions. The chiral liquid crystal compounds are represented by the following formula:

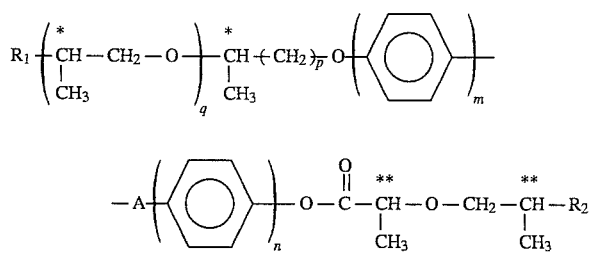

wherein:
$R_1$ is a $C_2$ to $C_{10}$ alkyl group, $R_2$ is a $C_2$ to $C_8$ alkyl group; A is either

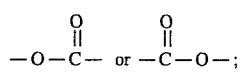

m is an integer of 1 or 2;
n is an integer of 1 or 2;
p and q are integers of 0 or 1, provided that when p=0, q=0, and p=1, q=1; and
\* and \*\* indicate, independently of each other, S- or R-stereoisomeric structure.

12 Claims, 3 Drawing Sheets

CHIRAL LIQUID CRYSTAL MATERIALS AS DOPANT FOR FERROELECTRIC LIQUID CRYSTAL COMPOSITIONS

FIELD OF THE INVENTION

This invention relates to a family of ferroelectric liquid crystal materials for use in electro-optical and display device applications. More particularly, this invention relates to a family of novel chiral liquid crystal materials for use as dopants to be mixed with a liquid crystal host material, which may or may not be composed of chiral molecules, to form ferroelectric liquid crystal compositions.

BACKGROUND OF THE INVENTION

As a result of the rapid development of liquid crystal display technologies, liquid crystal display devices have been utilized in a wide variety of applications. Liquid crystal display devices require low voltage and low power of operations, both of these advantageous factors enable them to be the most promising of the non-emissive electro-optical display candidates. Traditionally, liquid crystal displays are used in devices that require compact, energy-efficient voltage-controlled light switches, such as watch and calculator displays. More recently, liquid crystal displays have been increasingly used in large area computer display screens, as well as flat screen TV's. Conventional liquid crystal display devices are based on the dielectric alignment effects in nematic liquid crystal compounds. By virtue of dielectric anisotropy, the average molecular long axis of the liquid crystal compound takes up a preferred orientation in an applied electric field. However, because the coupling to an applied electric field by this mechanism is relatively weak, the resultant electro-optical response time may be too slow for more complicated applications. The conventional liquid crystal displays also do not provide adequate or desired contrast and wide enough view-angle for many potential applications.

The existence of ferroelectric liquid crystals was first observed in 1974 which was subsequently published in 1975 by R. B. Meyer, L. Liebert, L. Strzelecki, and P. Keller (see *J. Physique Letters,* 1975, 36, L-69). They reported that strong ferroelectricity could be observed from liquid crystals belonging to a chiral smectic C phase (Sc* phase). Prior to the discovery by Meyer, ferroelectricity was observed only in inorganic salt crystals. Meyer and his coworkers believed that ferroelectricity may be observed in optically active compounds with a tilted smectic liquid crystal phase. They synthesized a liquid crystal compound (S)-4-n-decyloxybenzylideneamino-2'-methylbutyl cinnamate (DOBAMBC) to prove their theory. Therefore, in theory, any optically active compound that exhibits tilted smectic phase can possess ferroelectricity. Currently, the chiral smectic C-phase (Sc*) compounds are receiving the most attention.

In 1980, N. A. Clark and S. T. Lagerwall proposed a liquid crystal light valve system wherein an optical switching phenomenon of a ferroelectric liquid crystal was utilized. (See Appl. Phys. Lett., 1980, 36, 899; see, also, U.S. Pat. No. 4,367,924, entitled "Chiral Smectic C or H Liquid Crystal Electro-Optical Device"). The discovery of Clark and Lagerwall opened the door for ferroelectric liquid crystals to be used in practical applications. One of the improvements advanced from their discovery is the use of surface stabilized ferroelectric liquid crystal device (SSFLCD) as a operating mechanism.

Chiral smectic C phase (Sc*) compounds possess a spontaneous ferroelectric polarization, or macroscopic dipole moment, derived from a dissymmetry in the orientation of molecular dipoles in the liquid crystal phase. Upon an appropriate application of an external electric field, the molecules in the ferroelectric liquid crystal phase will be aligned with the applied field. When the sign of the applied field is reversed, a "switching" of the ferroelectric liquid crystal molecules occurs. This switch can be employed for light modulation. It has been reported in the art that, over a wide range of electric field strengths, the response time ($\tau$) of a ferroelectric liquid crystal display is inversely proportional to the strength of the applied field (E) and the spontaneous polarization of the ferroelectric liquid crystal molecule (Ps), and is proportional to the rotational viscosity ($\eta$), as described in the following relationship:

$$\tau = \eta/(Ps \times E) \tag{1}$$

In Eqn. (1), $\eta$ is the viscosity of the ferroelectric liquid crystal, and E is the externally applied electrical voltage. From Eqn. (1), it is apparent that the response time of a ferroelectric liquid crystal can be reduced through appropriate molecular design to emphasize certain desired molecular characteristics. For example, a proper increase in the dipole moment of the ferroelectric molecule can increase the spontaneous polarization thereof and thus reduce the response time.

Ferroelectric liquid crystal materials are the key component of a ferroelectric liquid crystal display device. In practical applications, however, a single ferroelectric liquid crystal material may not provide all the desired properties for an intended ferroelectric liquid crystal display device. Therefore, it has been disclosed that a chiral liquid crystal compound can be used as a dopant to mix with a liquid crystal host material, which may or may not be composed of chiral molecules, to form a ferroelectric liquid crystal mixture. Addition of the dopant can affect the spontaneous polarization and the viscosity of the chiral smectic phase, and thereby directly affect the response time as indicated by Eqn. (1).

U.S. Pat. No. 4,923,633 discloses a chiral liquid crystal dopant composition for use in a ferroelectric smectic liquid crystal composition having a structure which contains two chiral centers from alpha hydroxy carboxylic acid groups. U.S. Pat. No. 5,130,048 discloses another chiral liquid crystal dopant composition containing a pair of 2,4-dihalobutanediol chiral units. Both compounds involve relatively complicated synthesis procedures, and they do not provide adequate increase in the spontaneous polarization of the ferroelectric liquid crystal materials.

SUMMARY OF THE INVENTION

The primary object of the present invention is to provide an optically and chemically stable chiral liquid crystal composition having high spontaneous polarization (about 300 nc/cm$^2$) so as to allow it for use as an effective dopant to be mixed with a chiral or achiral liquid crystal host material to form a ferroelectric liquid crystal composition, which provides many of the desired properties as a liquid crystal display material.

The chiral liquid crystal composition disclosed in the present invention is a molecule which contains a multiplicity of chiral centers and can be represented by the following formula:

wherein $R_1$ is a $C_2$ to $C_{10}$ alkyl group, $R_2$ is a $C_2$ to $C_8$ alkyl group;

A is either m is an integer of 1 or 2;

n is an integer of 1 or 2;

p and q are integers of 0 or 1, provided that when p=0, q=0, and p=1, q=1; and

* and ** both indicate, independently, S- or R-stereoisomeric structure.

The chiral liquid crystal dopant composition disclosed in the present invention is prepared by attaching a chiral organic acid and a chiral alcohol to the two terminal ends of a liquid crystal. A preferred example of the chiral organic acid is represented by the following formula:

Preferred examples of the chiral alcohol include the following two compounds:

One of the advantages of the present invention is that both the chiral organic acids and the chiral alcohols used for preparing the chiral liquid crystal dopant composition provide their own spontaneous polarization, thus both contribute to the spontaneous polarization of the dopant compound. As indicated in Eqn. (1), a higher value of spontaneous polarization will result in a more favorable response time, and therefore a more effective dopant composition.

BRIEF DESCRIPTION OF THE DRAWING

The present invention will be described in detail with reference to the drawings showing the preferred embodiment of the present invention, wherein.

DETAILED DESCRIPTION OF THE PREFERRED EMBODIMENT

The present invention discloses a dopant composition to be added to a chiral or achiral liquid crystal host material to form ferroelectric liquid crystal compositions, the dopant composition is represented by the following formula:

(Formula I)

wherein $R_1$ is a $C_2$ to $C_{10}$ alkyl group, $R_2$ is a $C_2$ to $C_8$ alkyl group;

A is either m is an integer of 1 or 2;

n is an integer of 1 or 2;

p and q are integers of 0 or 1, provided that when p=0, q=0, and p=1, q=1; and

* and ** both indicate, independently, S- or R-stereoisomeric structure.

The dopant composition disclosed in the present invention can be a compound represented by the above listed formula, or a mixture containing the same. The dopant composition can be mixed with a liquid crystal material mixture possessing a smectic C phase ($S_C$), or a liquid crystal material mixture possessing a chiral smectic C phase ($S_C^*$). The chiral liquid crystal dopant compound disclosed in the present invention contains a plurality of chiral centers, it will impart favorable ferroelectric liquid crystal characteristics when admixed with a liquid crystal host material to form a ferroelectric liquid crystal mixture.

The chiral liquid crystal dopant composition disclosed in the present invention is prepared from a chiral organic acid and a chiral alcohol. Since the chiral organic acid and the chiral alcohol each provides its own spontaneous polarization, a high value of spontaneous polarization can be obtained from the resultant molecule, thus an effective dopant composition is provided in the present invention.

The present invention will now be described more specifically with reference to the following examples. It is to be noted that the following descriptions of example including preferred embodiment of this invention are presented herein for purpose of illustration and description; it is not intended to be exhaustive or to limit the invention to the precise form disclosed.

EXAMPLE 1

Preparation of 4-{2(S)-[2(S)-methylbutoxy]propionyloxy-phenyl-4-{4'-2(S)-[2(S)-methylbutoxy]propoxy}phenyl benzoate (Compound I-a)

Compound I-a is represented by the following formula:

(Compound I-a)

Comparing Formula I above, Compound I-a has the following parameters: m=2, n=1, p=1, q=1, $R_1=C_2H_5$, $R_2=C_2H_5$,

*=S, and **=S.

Figure 1:
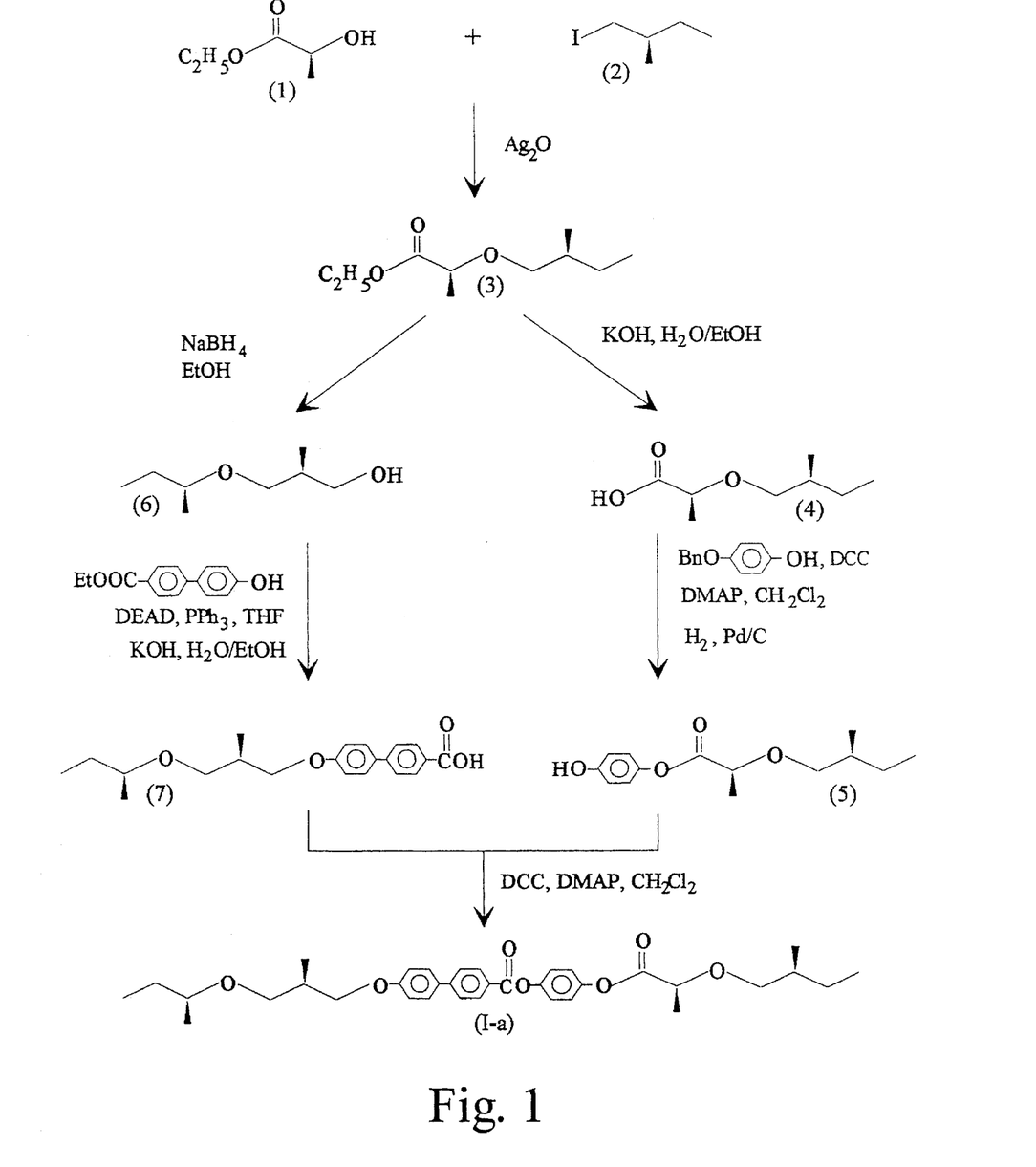
FIG. 1 is a flowchart diagram illustrating the synthesis of a first preferred embodiment of the chiral liquid crystal dopant of the present invention.

FIG. 1 shows a flowchart diagram illustrating the steps in synthesizing Compound I-a. First, 5.9 g of ethyl lactate (1), 11.90 g of (S)-1-iodo-2-methyl butane (2) and 13.8 g of silver oxide were added to a reactor and reacted at a temperature of about 50° C. and under an ultrasonic vibration for 12 hours. The reactant mixture was diluted and filtered with ether (50 ml×4). Then 5% of sodium hydroxide (50 ml×2) and water (50 ml×2) were used to rinse the organic layer, to which magnesium sulfate was afterward added to remove water. After filtration and concentration, the preliminary reaction product was purified by medium pressure liquid chromatography (MPLC) using silica gel and an eluent (n-hexane/ethyl acetate=15/1). The product, which is ethyl-2(S)-[2(S)-methylbutoxy]lactate (3), was weighed to be 3.90 g, representing a yield of 40%.

3.30 g of ethyl-2(S)-[2(S)-methylbutoxy]lactate (3) obtained from the above reaction, 2.20 g of sodium hydroxide, 20 ml of ethanol and 50 ml of water were added to a reactor, heated under reflux for one hour, and concentrated to remove ethanol. Thereafter, the reaction mixture was placed in an ice bath and neutralized with 10% of HCl, and extracted with dichloromethane (80 ml×2). The organic layer was dried with magnesium sulfate and concentrated. The reaction product was 2.70 g of 2(S)-[2(S)-methylbutoxy]lactic acid (4); and the reaction yield was 93%.

0.80 g of 2(S)-[2(S)-methylbutoxy]lactic acid (4) from the above reaction, 0.85 g of 4-phenylmethoxy phenol, 0.06 g of dimethylaminopyridine (DMAP), 1.09 g of dicyclohexyl carbodiimide (DCC) and 10 ml of dichloromethane were mixed at 25° C. and stirred for 12 hours. After concentration and column liquid chromatography (silica gel, n-hexane/ethyl acetate=4/1), 1.50 g of a solid product was obtained. The reaction yield was 86%. The solid product was mixed with 0.38 g ofPd/C (10%) to undergo a hydrogenation reaction. After the removal of Pd/C by filtration, and concentration, 1.02 of a liquid product (5)was obtained. The overall reaction yield was 93%.

In a separate reaction, 2.70 g of ethyl lactate (3) was dissolved into 25 ml of ethanol. After the addition of 1.00 g of sodium borohydride, the reaction mixture was heated under reflux for 4 hours. Then, the reaction mixture was cooled down and 10 ml water was added and stirred for 10 minutes. The organic layer was extracted with ether (100 ml×3) and dried and concentrated with magnesium sulfate. Thereafter, it was purified by column liquid chromatography (silica gel, and n-hexane/ethyl acetate=5/1), and 1.57 g of product, which is 2(S)-[2(S)-methylbutoxy]propyl alcohol (6) was obtained. The reaction yield was 75%.

0.60 g of 2(S)-[2(S)-methylbutyloxy]propyl alcohol (6) from the above reaction, 1.04 g of ethyl p-hydroxybiphenyl carboxylate and 1.31 g of triphenylphosphine were added to 10 ml of tetrahydrofuran. Under nitrogen and in an ice bath, 0.87 g of diethyl azodicarboxylate (DEAD) and 5 ml of tetrahydrofuran were gradually added to the reaction mixture. After the temperature was returned to 25° C., the reaction mixture was stirred for 12 hours. After drying and purification by column liquid chromatography (silica gel and n-hexane/ethyl acetate/trichloromethane=6/1/3), 0.99 g of a solid product was obtained, representing a reaction yield of 65%. 0.60 g of the solid product was added to solution containing 0.18 g of potassium hydroxide, 20 ml ethanol and 10 ml water, and heated trader reflux for one hour. After filtration and concentration, and crystallization with ethanol, 0.54 g of solid product (7) was obtained, representing a reaction yield of 95%.

Finally, 120 mg of solid product (7), 97 mg of liquid product (5), 5 mg of dimethylaminopyridine, 145 mg of dicyclohexyl carbodiimide and 3 ml of dichloromethane were mixed and stirred at 25° C. for 12 hours. After concentration and purification by column liquid chromatography (silica gel, n-hexane/ethyl acetate/trichloromethane= 6/1/3), 125 mg of final product (Compound I-a) was obtained, representing a reaction yield of 62%. The analytical results obtained from compound I-a are summarized below:

$[\alpha]_D^{25}=-42°$ (c=1.00, $CHCl_3$) $^1H$ NMR ($CDCl_3$) δ:

| δ | 8.2 | 7.6 | 7.2 | 7.0 | 4.2 | 4.0–3.6 | 3.55 | 3.40 | 3.30 | 1.9–1.1 | 1.0–0.85 |
|---|-----|-----|-----|-----|-----|---------|------|------|------|---------|----------|
| H | 2H  | 4H  | 2H  | 2H  | 1H  | 3H      | 1H   | 2H   | 1H   | 14H     | 10H      |

EXAMPLE 2

Preparation of
4'-{2(S)-[2(S)-methylbutoxy]propoxy}biphenyl-4'-
{2(S)-[2(S)-methyl-butoxyl]propionyloxy}benzoate
(Compound I-b)

Compound I-b is represented by the following formula:

Finally, 81 mg of solid product (8), 84 mg of solid product (9) were mixed and reacted under conditions similar to those in Example 1 to effect an esterification reaction. 83 mg of a final product (Compound I-b) was obtained, representing a reaction yield of 55%. The analytical results obtained from compound I-b are summarized below:

$[\alpha]_D^{25} = -46.5°$ (c=1.01, CHCl$_3$) $^1$H NMR (CDCl$_3$) δ:

(Compound I-b)

Comparing Formula I above, Compound I-b has the following parameters: m=2, n=1, p=1, q=1, R$_1$=C$_2$H$_5$, R$_2$=C$_2$H$_5$,

*=S, and **=S.

| δ | 8.2 | 7.6 | 7.2 | 7.0 | 4.2 | 4.0–3.6 | 3.55 | 3.4–3.3 | 1.9–1.1 | 1.0–0.85 |
|---|---|---|---|---|---|---|---|---|---|---|
| H | 2H | 4H | 4H | 2H | 1H | 3H | 1H | 3H | 14H | 10H |

Figure 2:
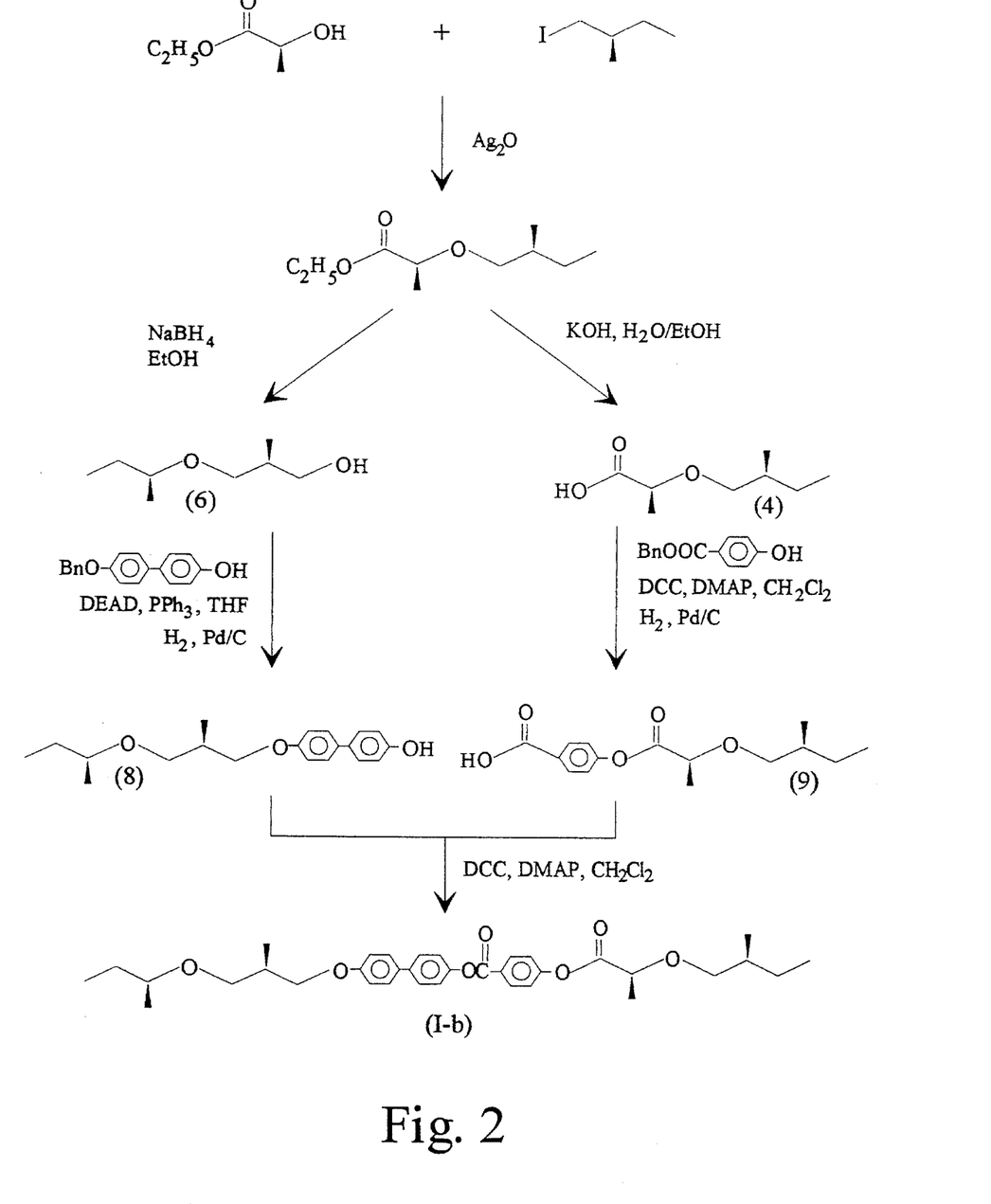
FIG. 2 is a flowchart diagram illustrating the synthesis of a second preferred embodiment of the chiral liquid crystal dopant of the present invention.

FIG. 2 shows a flowchart diagram illustrating the steps in synthesizing Compound I-b. The first portion of FIG. 2 is identical to FIG. 1. The differences are described in detail below.

0.29 g of liquid (6) and 0.63 g of triphenyl phosphine were dissolved in 5 ml of ether. Under nitrogen and in an ice bath, a solution containing 0.42 g of diethyl azodicarboxylate in 5 ml of ether was gradually added to the reaction mixture. The temperature was then returned to 25° C. and the reaction mixture was stirred for 12 hours. After concentration and purification with column liquid chromatography (silica gel and n-hexane/ethyl acetate/dichloromethane=10/1/2), the raw reaction product was re-crystallized with ethanol to obtain 0.24 g of product, representing a reaction yield of 30%. The solid reaction product was mixed with 85 mg of 10% Pd/C to effect a hydrogenation reaction. The Pd/C was removed by filtration. After concentration, 0.19 g of solid product (8) was obtained; the reaction yield was 70%.

In a separate reaction, 0.80 g of liquid (4), 1.25 g of benzyl 4-hydroxybenzoate, 0.06 g of p-dimethylaminopyridine 1.09 g of dicyclohexyl carbodiimide and 10 ml of dichloromethane were mixed and stirred at 25° C. for 12 hours. After concentration and purification with column liquid chromatography (silica gel and n-hexane/ethyl acetate/trichloromethane=6/1/3), 1.38 g of an intermediate product was obtained, representing a reaction yield of 62%. 0.41 g of the intermediate reaction product was mixed with 0.10 g of 10% Pd/C to effect a hydrogenation reaction. The Pd/C was removed by filtration. After concentration, 0.24 g of solid product (9) was obtained; the reaction yield was 80%.

EXAMPLES 3–5

(Preparation of Compounds I-c, I-d and I-e)

Liquid crystal compounds I-c, I-d, and I-e, which are similar to liquid crystal compounds I-a and I-b, were prepared in procedures similar to those described above. Their molecular structures are summarized in Table 1.

EXAMPLE 6

(Preparation of liquid crystal mixtures)

10 mol % of the liquid crystals I-a through I-e obtained from the above examples were respectively added to a host liquid crystal material W82 (obtained from Aldrich, catalog number 32,792-1), which has a spontaneous polarization Ps of close to zero. After thorough mixing, the liquid crystal properties and spontaneous polarization were measured in accordance with the methods disclosed by Martinot-Lagarde, J. Phys., 37, C-3 p129 (1976). The Ps (extrapolated) values of these compounds were extrapolated from the 10 mol % values, respectively. Results of these tests are summarized in Table 1.

EXAMPLE 11

(Preparation of
4-{2(S)-[2(S)-methylbutoxy]propionyloxy}biphenyl-4-
[2(S)-octoxy]benzoate (Compound I-h)

Compound I-h is represented by the following formula:

(Compound I-h)

Comparing Formula I above, Compound I-h has the following parameters: m=1, n=2, p=0, q=0, $R_1=C_2H_5$, $R_2=C_6H_{13}$,

*=S, and **=S.

Figure 3:
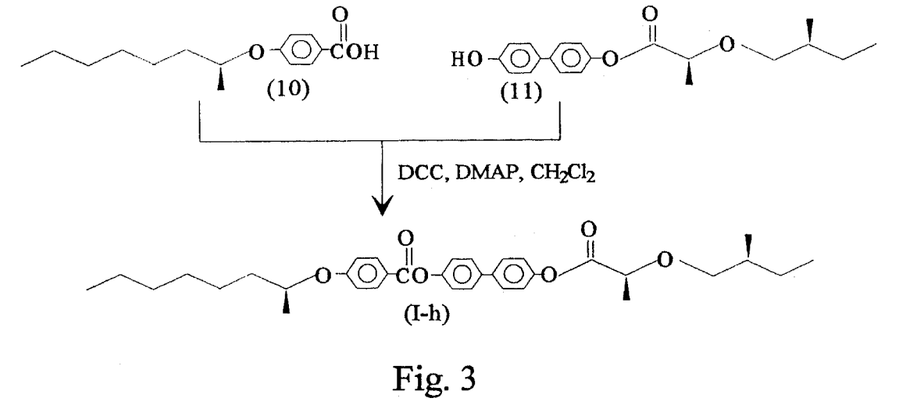
FIG. 3 is a partial flowchart diagram illustrating the synthesis of a third preferred embodiment of the chiral liquid crystal dopant of the present invention.

FIG. 3 shows a partial flowchart diagram illustrating the steps in synthesizing Compound I-h. Most of the synthesis steps are similar to those in FIGS. 1 and 2. In the preparation of Compound I-h, 0.26 g of 4-[2(S)-octoxy]benzoic acid (10) and 0.33 g of 4-hydroxybiphenyl-2(S)-[2(S)-methylbutoxy]propionate (11) were mixed and reacted under conditions similar to those described in Example 1. After the completion of the reaction 0.28 g of final product (I-h) was obtained, representing a reaction yield of 50%. The analytical results obtained from compound I-h are summarized below:

$[\alpha]_D^{25}=-25.7°$ (c=1.01, CHCl$_3$) $^1$H NMR (CDCl$_3$) δ:

| δ | 8.2 | 7.6 | 7.2 | 7.0 | 4.4 | 4.2 | 3.6 | 3.3 | 1.9–1.1 | 1.0–0.85 |
|---|---|---|---|---|---|---|---|---|---|---|
| H | 2H | 4H | 4H | 2H | 1H | 1H | 1H | 1H | 20H | 8H |

EXAMPLE 12

Preparation of
4-[2(R)octoxyl}phenyl-4-{4'-[2(S)-(2(S)-methylbutoxy]propionyloxy]phenyl benzoate (Compound I-o)

Compound I-o is represented by the following formula:

(Compound I-o)

Comparing Formula I above, Compound I-o has the following parameters: m=1, n=2, p=0, q=0, $R_1=C_2H_5$, $R_2=C_6H_{13}$,

*=R, and **=S.

Figure 4:
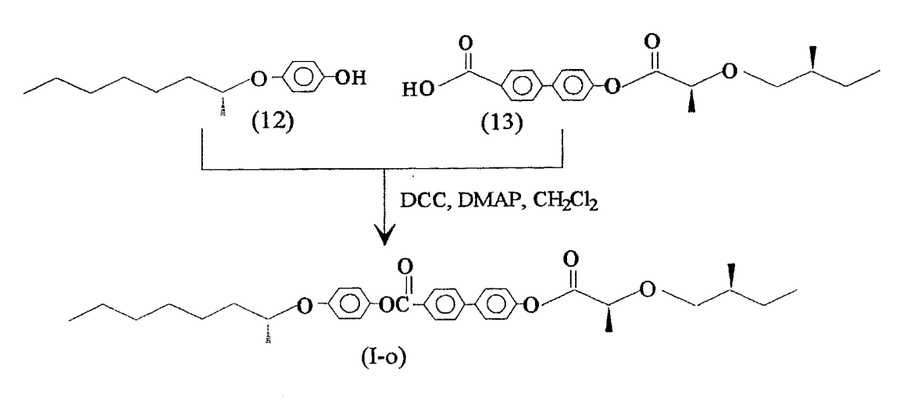
FIG. 4 is a partial flowchart diagram illustrating the synthesis of a fourth preferred embodiment of the chiral liquid crystal dopant of the present invention.

FIG. 4 shows a partial flowchart diagram illustrating the steps in synthesizing Compound I-o. Most of the synthesis steps are similar to those in FIGS. 1 and 2. In the preparation of Compound I-o, 110 mg of 4-[2(R)-octoxy]phenol (12) and 178 mg of 4-{4'-[2(S)-( 2(S)-methylbutoxy)propionyloxy]phenyl benzoic acid were mixed and reacted under conditions similar to those described in Example 1. 170 mg of a final product (I-o) was obtained, representing a reaction yield of 60%. The analytical results obtained from compound I-o are summarized below:

$[\alpha]_D^{25}=-25.7°$ (c=1.00, CHCl$_3$) $^1$H NMR (CDCl$_3$) δ:

| δ | 8.2 | 7.7 | 7.2 | 6.9 | 4.4 | 4.2 | 3.6 | 3.3 | 1.9–1.0 | 1.0–0.85 |
|---|---|---|---|---|---|---|---|---|---|---|
| H | 2H | 4H | 4H | 2H | 1H | 1H | 1H | 1H | 20H | 8H |

EXAMPLES 13–18

(Preparation of Ferroelectric liquid Crystal Dopants I-f, I-g I-i, I-j, I-k, I-l, I-m and I-p)

Liquid crystal compounds I-f, I-g I-i, I-j, I-k, I-l, I-m and I-p, which are similar to liquid crystal compounds I-h and I-o, were prepared in procedures similar to those described above. Their molecular structures are summarized in Table 2.

EXAMPLE 19–28

(Preparation of liquid crystal mixtures)

10 mol % of the liquid crystals I-f, I-g, I-h, I-i, I-j, I-k, I-l, I-m, I-o and I-p obtained from the above examples were respectively added to a host liquid crystal material W82 (obtained from Aldrich, catalog number 32,792-1), which has a spontaneous polarization Ps of close to zero, to form liquid crystal mixtures. After thorough mixing, the liquid crystal properties and spontaneous polarization were measured in accordance with the methods disclosed by Martinot-Lagarde, *J. Phys.*, 37, C-3 p129 (1976). The Ps (extrapolated) values of these compounds were extrapolated from the 10 mol % values, respectively. Results of these tests are summarized in Table 2.

EXAMPLE 29

(Preparation of an achiral liquid crystal mixture)

The following achiral liquid crystal compounds are mixed according to the stated molar ratios:

| Liquid Crystal Compound | Mol % |
|---|---|
|  | 23 |
|  | 13 |
|  | 56 |
|  | 8 |

The phase transition temperatures of the above liquid crystal mixture were measured below:

$$K(3° C.)S_C(64° C.)S_A(74° C.)N(78° C.)I$$

EXAMPLE 30

(Preparation of a chiral liquid crystal mixture)

20 wt % of chiral liquid crystal compound I-d was added to the achiral liquid crystal mixture prepared from Example 29 which possessed a smectic C-phase. The resultant mixture exhibited the characteristic of a ferroelectric liquid crystal composition as indicated by the presence of the chiral smectic C-phase $S_C^*$. The phase transition temperatures and response time of the chiral liquid crystal mixture were measured and reported below:

$$K(-9° C.)S_C^*(63° C.)S_A(68° C.)N(72° C.)I$$

Response Time: 52 microseconds

Applied Field: ±15 volt

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 1

$$R_1 \left( \overset{*}{\underset{CH_3}{CH}} - CH_2 - O \right)_q \overset{*}{\underset{CH_3}{CH}} (CH_2)_{\overline{p}} O \left[ \left\langle\bigcirc\right\rangle_m - A - \left\langle\bigcirc\right\rangle \right]_n O - \overset{O}{\underset{}{\overset{\|}{C}}} - \overset{}{\underset{CH_3}{CH}} - O - CH_2 - \overset{}{\underset{CH_3}{CH}} - R_2$$

| Liquid Crystal | m | n | p | q | $R_1$ | $R_2$ | A | * | ** | Ps(extrapolated) | Liquid Crystal Phases (10 mol %) |
|---|---|---|---|---|---|---|---|---|---|---|---|
| I-a | 2 | 1 | 1 | 1 | $C_2H_5$ | $C_2H_5$ | $CO_2$ | S | S | 90 | $K \xleftarrow{17°} S_c^* \xleftarrow{65°} N^* \xleftarrow{69°} I$ |
| I-b | 2 | 1 | 1 | 1 | $C_2H_5$ | $C_2H_5$ | $O_2C$ | S | S | 240 | $K \xleftarrow{17°} S_c^* \xleftarrow{61°} N^* \xleftarrow{66°} I$ |
| I-c | 1 | 2 | 1 | 1 | $C_2H_5$ | $C_2H_5$ | $CO_2$ | S | S | 120 | $K \xleftarrow{16°} S_c^* \xleftarrow{62°} N^* \xleftarrow{68°} I$ |
| I-d | 1 | 2 | 1 | 1 | $C_2H_5$ | $C_2H_5$ | $O_2C$ | S | S | 300 | $K \xleftarrow{17°} S_c^* \xleftarrow{64°} N^* \xleftarrow{69°} I$ |
| I-e | 1 | 1 | 1 | 1 | $C_2H_5$ | $C_2H_5$ | $CO_2$ | S | S | — | |

TABLE 2

| Liquid Crystal | m | n | p | q | $R_1$ | $R_2$ | A | * | ** | Ps(extrapolated) | Liquid Crystal Phases (10 mol %) |
|---|---|---|---|---|---|---|---|---|---|---|---|
| I-f | 2 | 1 | 0 | 0 | $C_2H_5$ | $C_6H_{15}$ | $CO_2$ | S | S | 80 | $K \xleftarrow{22°} S_c^* \xleftarrow{56°} N^* \xleftarrow{66°} I$ |
| I-g | 2 | 1 | 0 | 0 | $C_2H_5$ | $C_6H_{15}$ | $O_2C$ | S | S | 75 | $K \xleftarrow{10°} S_c^* \xleftarrow{50°} N^* \xleftarrow{56°} I$ |
| I-h | 1 | 2 | 0 | 0 | $C_2H_5$ | $C_6H_{15}$ | $CO_2$ | S | S | 55 | $K \xleftarrow{10°} S_c^* \xleftarrow{50°} N^* \xleftarrow{56°} I$ |
| I-i | 1 | 2 | 0 | 0 | $C_2H_5$ | $C_6H_{15}$ | $O_2C$ | S | S | 55 | $K \xleftarrow{17°} S_c^* \xleftarrow{62°} N^* \xleftarrow{66°} I$ |
| I-j | 1 | 1 | 0 | 0 | $C_2H_5$ | $C_6H_{15}$ | $CO_2$ | S | S | — | |
| J-k | 2 | 1 | 0 | 0 | $C_2H_5$ | $C_6H_{15}$ | $CO_2$ | R | S | 210 | $K \xleftarrow{25°} S_c^* \xleftarrow{66°} N^* \xleftarrow{71°} I$ |
| I-l | 2 | 1 | 0 | 0 | $C_2H_5$ | $C_6H_{15}$ | $O_2C$ | R | S | 197 | $K \xleftarrow{20°} S_c^* \xleftarrow{63°} N^* \xleftarrow{67°} I$ |
| I-m | 1 | 2 | 0 | 0 | $C_2H_5$ | $C_6H_{15}$ | $CO_2$ | R | S | 230 | $K \xleftarrow{16°} S_c^* \xleftarrow{65°} N^* \xleftarrow{67°} I$ |
| I-o | 1 | 2 | 0 | 0 | $C_2H_5$ | $C_6H_{15}$ | $O_2C$ | R | S | 160 | $K \xleftarrow{16°} S_c^* \xleftarrow{67°} N^* \xleftarrow{70°} I$ |
| I-p | 1 | 1 | 0 | 0 | $C_2H_5$ | $C_6H_{15}$ | $CO_2$ | R | S | — | |

What is claimed is:

1. A ferroelectric liquid crystal dopant represented by the following formula:

wherein:

$R_1$ is a $C_2$ to $C_{10}$ alkyl group, $R_2$ is a $C_2$ to $C_8$ alkyl group;

A is either $$-O-\overset{O}{\underset{\|}{C}}- \quad \text{or} \quad -\overset{O}{\underset{\|}{C}}-O-;$$

m is an integer of 1 or 2;

n is an integer of 1 or 2;

p and q are integers of 0 or 1, provided that when p=0, q=0, and p=1, q=1; and

* and ** indicate, independently of each other, S- or R-stereoisomeric structure.

2. The ferroelectric liquid crystal dopant according to claim 1 wherein $R_1$ is a $C_2$ to $C_6$ alkyl group.

3. The ferroelectric liquid crystal dopant according to claim 1 wherein $R_2$ is a $C_2$ to $C_6$ alkyl group.

4. The ferroelectric liquid crystal dopant according to claim 1 which is represented by the following formula:

wherein * and ** indicate, independently of each other, S- or R-stereoisomeric structure.

5. The ferroelectric liquid crystal dopant according to claim 1 which is represented by the following formula:

wherein * and ** indicate, independently of each other, S- or R-stereoisomeric structure.

6. The ferroelectric liquid crystal dopant according to claim 1 which is represented by the following formula:

wherein * and ** indicate, independently of each other, S- or R-stereoisomeric structure.

7. The ferroelectric liquid crystal dopant according to claim 1 which is represented by the following formula:

wherein * and ** indicate, independently of each other, S- or R-stereoisomeric structure.

8. The ferroelectric liquid crystal dopant according to claim 1 which is represented by the following formula:

wherein * and ** indicate, independently of each other, S- or R-stereoisomeric structure.

9. The ferroelectric liquid crystal dopant according to claim 1 which is represented by the following formula:

wherein * and ** indicate, independently of each other, S- or R-stereoisomeric structure.

10. The ferroelectric liquid crystal dopant according to claim 1 which is represented by the following formula:

wherein * and ** indicate, independently of each other, S- or R-stereoisomeric structure.

11. The ferroelectric liquid crystal dopant according to claim 1 which is represented by the following formula:

wherein * and ** indicate, independently of each other, S- or R-stereoisomeric structure.

12. A ferroelectric liquid crystal composition comprising an achiral smectic C liquid crystal compound and a dopant, said dopant being represented by the following formula:

wherein:

$R_1$ is a $C_2$ to $C_{10}$ alkyl group, $R_2$ is a $C_2$ to $C_8$ alkyl group;

A is either $$-O-\overset{O}{\underset{\|}{C}}- \text{ or } -\overset{O}{\underset{\|}{C}}-O-;$$

m is an integer of 1 or 2;

n is an integer of 1 or 2;

p and q are integers of 0 or 1, provided that when p=0, q=0, and p=1, q=1; and

* and ** indicate, independently of each other, S- or R-stereoisomeric structure.

* * * * *